US007928279B2

(12) United States Patent
Rosenberg

(10) Patent No.: US 7,928,279 B2
(45) Date of Patent: Apr. 19, 2011

(54) ANTI-INFLAMATORY PAD

(76) Inventor: Lior Rosenberg, Omer (IL)

( * ) Notice: Subject to any disclaimer, the term of this patent is extended or adjusted under 35 U.S.C. 154(b) by 1420 days.

(21) Appl. No.: 10/182,498

(22) PCT Filed: Jan. 25, 2001

(86) PCT No.: PCT/IL01/00072
§ 371 (c)(1),
(2), (4) Date: Dec. 2, 2002

(87) PCT Pub. No.: WO01/54743
PCT Pub. Date: Aug. 2, 2001

(65) Prior Publication Data
US 2003/0187377 A1    Oct. 2, 2003

(30) Foreign Application Priority Data
Jan. 27, 2000  (IL) .......................................... 134269

(51) Int. Cl.
*A61F 5/24*     (2006.01)
*A61F 5/28*     (2006.01)
*A61F 13/00*    (2006.01)
*A61F 15/00*    (2006.01)

(52) U.S. Cl. ................ 602/48; 602/42; 602/43; 602/56; 128/95.1; 128/96.1; 128/98.1; 128/102.1

(58) Field of Classification Search ............... 602/48–51, 602/53–58, 42–43; 424/443–449; 606/197; 604/358–402; 128/95.1, 98.1, 99.1, 100.1, 128/106.1, 112.1, 113.1, 96.1, 101.1, 102.1, 128/114.1; 600/38–40; 607/108
See application file for complete search history.

(56) References Cited

U.S. PATENT DOCUMENTS

| | | | | |
|---|---|---|---|---|
| 1,640,416 A * | 8/1927 | MacDonald | ................ | 128/98.1 |
| 1,989,686 A * | 2/1935 | Deutsch | ........................ | 604/398 |
| 2,615,445 A * | 10/1952 | Holmes | ........................ | 128/98.1 |
| 3,882,870 A * | 5/1975 | Hathaway | ..................... | 604/392 |
| 3,993,074 A * | 11/1976 | Murray et al. | ................ | 604/369 |
| 4,040,424 A | 8/1977 | Hunt | | |
| 4,097,943 A * | 7/1978 | O'Connell | ........................ | 5/484 |
| 4,484,919 A * | 11/1984 | Sohn et al. | ..................... | 604/358 |
| 4,505,707 A * | 3/1985 | Feeney | ........................... | 604/393 |
| 4,660,238 A | 4/1987 | Jay | | |
| 4,755,384 A | 7/1988 | Mallasz | | |
| 4,761,843 A | 8/1988 | Jay | | |
| 4,858,604 A * | 8/1989 | Konishi | ......................... | 602/57 |

(Continued)

OTHER PUBLICATIONS

Hemorrhoids and Varicose Veins: A Review of Treatment Options, Douglas McKay, ND Candidate 2001, Alternative Medicine Review, vol. 6, No. 2 2001 pp. 126-140.

*Primary Examiner* — Patricia M Bianco
*Assistant Examiner* — Brandon Jackson
(74) *Attorney, Agent, or Firm* — Reed Smith LLP

(57) ABSTRACT

A pad for the treatment of inflammatory afflictions, which comprise an absorbing matrix, a medicament that is a hypertonic substance such as inorganic salt solutions, and a functional backing for directing and limiting the activity of the medicament to the desired body surface. The pad may further comprise binding means for maintaining it in place and in engagement with the desired body surface. The absorbing matrix and the functional backing may be structurally connected or separate. The absorbing matrix may be made of cotton, lignin cellulose or synthetic absorbing materials.

27 Claims, 4 Drawing Sheets

U.S. PATENT DOCUMENTS

| | | | |
|---|---|---|---|
| 4,943,432 A * | 7/1990 | Biener | 424/647 |
| 5,196,405 A | 3/1993 | Packman | |
| 5,263,926 A * | 11/1993 | Wilk | 604/11 |
| 5,325,543 A * | 7/1994 | Allen | 2/406 |
| 5,695,456 A * | 12/1997 | Cartmell et al. | 602/43 |
| 5,733,275 A * | 3/1998 | Davis et al. | 604/387 |
| 5,898,037 A * | 4/1999 | Marx | 424/49 |
| 5,981,822 A * | 11/1999 | Addison | 602/41 |
| 6,040,493 A * | 3/2000 | Cooke et al. | 602/41 |
| 6,716,229 B2 * | 4/2004 | Toth | 606/197 |
| 2001/0003157 A1 * | 6/2001 | Toth | 606/197 |
| 2002/0012697 A1 * | 1/2002 | Schwartz | 424/450 |
| 2002/0147482 A1 * | 10/2002 | Carter | 607/108 |
| 2004/0162537 A1 * | 8/2004 | Manasek | 604/385.01 |
| 2004/0167479 A1 * | 8/2004 | Warren et al. | 604/289 |

\* cited by examiner

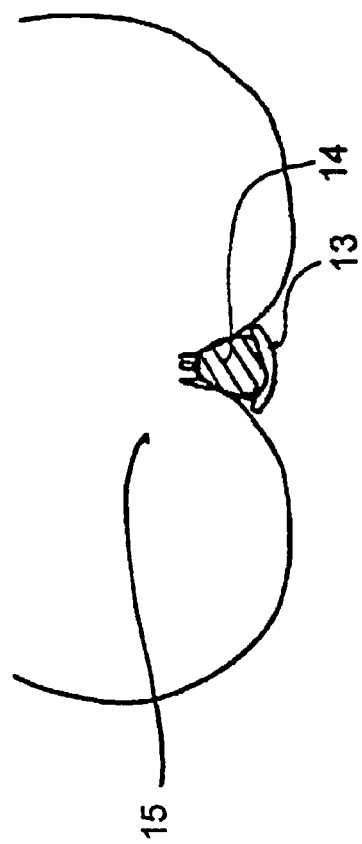
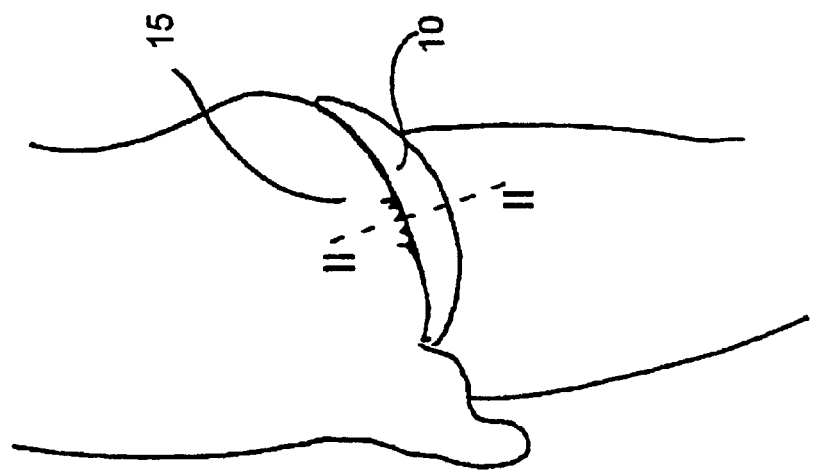

ANTI-INFLAMATORY PAD

FIELD OF THE INVENTION

The invention relates to an anti-inflammatory pad for use in the treatment of any inflammatory or swelling phenomenon, particularly but not exclusively, hemorrhoids.

BACKGROUND OF THE INVENTION

Inflammation and swelling are very common phenomena in daily life and in medicine. Hemorrhoids are a medical problem accompanied by very unpleasant manifestations, such as inflammation, swelling, exudates and pain. The treatment of any inflammatory and tumescent, edematous process (such as dermatitis, hemorrhoids or any localized infection) is divided into a conservative (local and/or systemic) treatment and a specific (sometimes even surgical) treatment. Obviously, the local conservative treatment is more frequently used than the systemic or surgical treatment.

A huge plethora of local treatments have been, and still are, in use today, from creams and ointments to dry or wet dressings containing various substances and medicaments. Some of the treatments depend on the topical application of hypertonic substances, such as magnesium sulfate and other salts or even sugar and honey. The use of hypertonic soaking solutions applied as irrigation on absorbing dressing is one of the commonest local treatment modality. This method can be easily used on many areas of the body, especially the limbs. The use of soaking dressing on the trunk or face, and especially on the perineum region is technically difficult and only occasionally attempted. The commonest method is using sitting baths of hypertonic solutions to bring the medicaments (salts, in this case) to the perineal region. All these treatment modalities are used for external problems and may be less effective in case of internal hemorrhoids or deep, subcutaneous inflammatory processes. In such cases, more invasive methods and devices, such as penetrative probes, should be used.

Hemorrhoid supporting pads are described in U.S. Pat. Nos. 4,660,238 and 4,761,843. They have only a mechanical function, rendering sitting less painful, but they provide no treatment of the hemorrhoid inflammation.

U.S. Pat. No. 4,040,424 describes a surgical absorbent pad that can be applied in hemorrhoidectomy procedures, but is not intended for medicating the affected area.

It is a purpose of this invention to provide a device, specifically a pad, for treating inflammatory and swelling phenomena, that is effective, simple, economical and easy to apply.

It is another purpose of this invention to provide such a pad that is particularly adapted for the treatment of hemorrhoids, especially the ones with external components.

It is a further purpose of this invention to provide such a pad that includes medicaments that are readily available and harmless.

Other purposes and advantages of this invention will appear as the description proceeds.

SUMMARY OF THE INVENTION

The goal of the invention is to combine and integrate the traditionally proven methods of bathing the inflamed area with hypertonic-hyperosmotic medicaments into an easy-to-apply, easy to function in daily life, cost-effective and disposable device.

The pad according to the invention comprises an absorbing matrix; a medicament that is a hyperosmotic-hypertonic solution such as inorganic salts; and a functional backing which is a layer that directs and limits the activity of the medicament to the desired body surface. Preferably, the pad of the invention is provided with binding means for maintaining it in place and in engagement with the desired body surface.

The absorbing matrix, the functional backing and the binding means may be structurally connected and constitute a unitary device, or may be separated and placed in cooperative positioned relationship when the pad is applied.

The matrix may be made of any absorbent material such as, for instance, cotton, lignin cellulose, gels or synthetic absorbing materials; in general, of such absorbing matrices as are presently used in diapers, hygienic pads and towels and the like. The material should be soft, easily conforming to the changing topography of the body areas. The feature of adaptiveness/conformability is very important, especially in the case of hemorrhoids pads, where it has to conform itself to individual anatomical differences of the perineal region. Obviously such material should be non-irritating and hypoalergenic. Suitable materials are well known in the art, and there is no need to further describe them.

The medicament is a hypertonic-hyperosmotic solution, e.g., of inorganic salts, preferably of alkali and/or earth-alkali metals, or are solutions of mixtures of such salts. The salts may be industrially produced and mixed, or they or their mixtures may be extracted from natural sources. Typical examples are 40 wt % to 70 wt % solutions of NaCl or $MgSO_4$. Another example of medicament that is particularly effective are solutions of salts which constitute the Dead Sea brines. Many prefer to use organic materials such as sugar or sugar products such as honey, for the same purpose.

Other components, such as other medically active components, steroids, minerals, vegetable or animal oils or lubricants of any kinds, and the like, may be added to the solution of salts as desired to form the medicaments of the invention.

The solution, that constitutes the medicament of the pad of the invention, preferably saturates the absorbing matrix, but does not exceed its absorbing capacity, to avoid the leakage of medicament solution beyond the limits of the functional backing and of the surrounding skin.

The composition of the medicament can be adjusted according to the particular conditions in which the pad of the invention is used, and particularly to the type of inflammatory disease which is to be treated, the part of the body concerned, etc.

The functional backing, which constitutes the outermost layer of the device, is preferably made of impermeable material, that is sufficiently soft and pliable to adapt to the changes in shapes and contours of the human body. Examples of suitable materials are films such as polyurethane, silicon or other plastic materials, or foil, such as aluminum or other non-toxic pliable electrically conductive metal alloys or materials. The electrically conductive backing may be used for electro- or ions phoresis methods for directional diffusion and ion exchange between the patient's body and the dressing. In specific cases, the functional backing may be made of semipermeable material, to allow for an exchange of gases and liquids with the environment. In some cases, particularly when the device of the invention is placed on a rather flat surface of the human body, the functional backing may be provided with an adhesive substance applied to the side on which the absorbent matrix is located, so as to adhesively retain such matrix. Another possible features of the functional backing will be described later on.

In this description and claims, the term "outer surface" means a surface that is not in contact with the body, when the pad is worn by a patient, and the term "inner surface" means a surface that is in contact with the body, when the pad is worn by a patient.

As has been said, the pad is preferably provided with a binding means. The binding means can be constituted by strings or ribbons, which can carry adhesive members, such as VELCRO® connectors or the like or adhesive layers, according to whether the pad is to be bound to an item of underwear or the surface of the body itself. The strings or ribbons are preferably elastic. They are preferably attached to the absorbing matrix though they could be attached to the functional backing. They can be substituted by protrusions of the matrix or the backing.

The functional backing may have edges extending beyond the absorbing matrix, and the inner side of said edges may be provided with a pressure-sensitive, bio-compatible adhesive.

The absorbing matrix may be thick and spongy to conform to irregular areas of the body, or flat to conform to flat areas, or tubular or banana-shaped to conform to the perineum.

The invention provides a medical device for the local treatment of inflamed, swollen areas, including difficult body regions, such as the perineum and hemorrhoids. The use and the simple application of the pad of the invention provides very fast relief of the local pains and irritations. Its continuous use also effects the shrinking and healing of the swollen area or piles. It has no side—or adverse effects, other than a mild dryness of the surrounding skin, that can easily be relieved by the application of some mineral oils or fatty ointments.

BRIEF DESCRIPTION OF THE DRAWINGS

In the drawings:

FIG. 1 is a schematic perspective illustration of a pad according to an embodiment of the invention;

FIG. 2 is a cross-section of FIG. 1 taken on plane II-II of FIG. 1;

DETAILED DESCRIPTION OF PREFERRED EMBODIMENTS

Figure 3B:
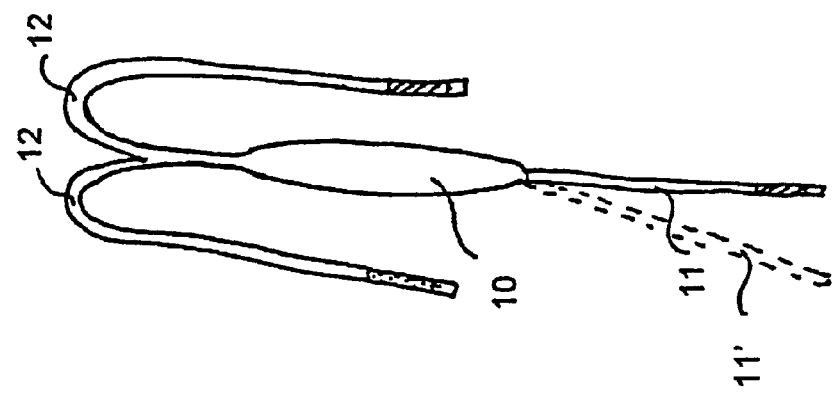
FIGS. 3A and 3B are schematic perspective illustrations of a pad similar to that of FIG. 1, but differently set in place.

FIGS. 1 and 2 illustrate an embodiment of an anti-inflammatory pad according to the invention, particularly intended for the treatment of hemorrhoids, generally indicated at 10. Because of the part of the body to which it is to be applied, which is generally indicated at 15, it is conveniently banana-shaped, as seen in the drawing.

FIG. 2 is a cross-section of pad 10 taken along plane II-II of FIG. 1, which shows that the pad comprises an outer impermeable layer of material, which in this case is seen to be a plastic film 13, and an absorbing matrix 14, which in this case is assumed to be made of cotton, lignin or such and which is saturated with a hypertonic solution of salts, which in this case is assumed to be a solution of Dead Sea salts or brines. The pad 10, because of its shape, could, in some cases, be held by the two buttocks and be used as such without being attached to the body in any other way, but it is preferred, as in FIGS. 3A and 3B, to provide it with strings or ribbons 11 and 12 for attaching it to the body.

Figure 3A:
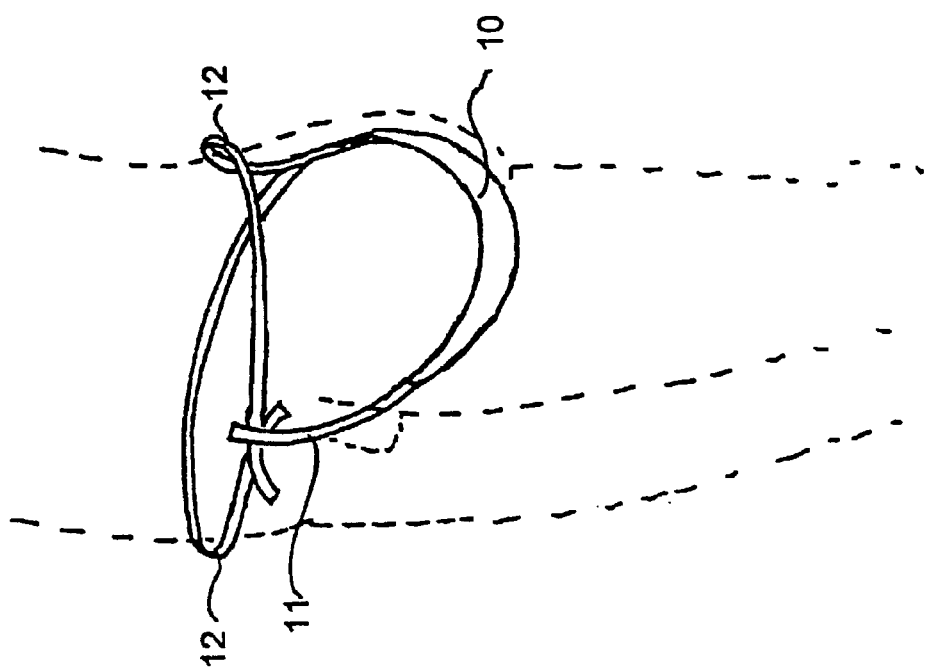

When the pad is set in place, strings or ribbons 11 are drawn upwards in front of the body and strings or ribbons 12 are drawn upwards on the rear of the body, or vice versa. The strings or ribbons are provided with means for removably attaching them to an item of clothing, or to each other, e.g., by VELCRO® connections, or are provided with adhesive pads for removably attaching them to the skin. Alternatively, as seen in FIG. 3A, in which the body is schematically indicated in broken lines, the strings or ribbons 11, 11' and 12 may be drawn partly along one side of the body and partly along the other side, and tied together to retain the pad 10 on both sides of the body. The same pad is illustrated in a vertical view, when not in place, in FIG. 3B.

Figure 4:
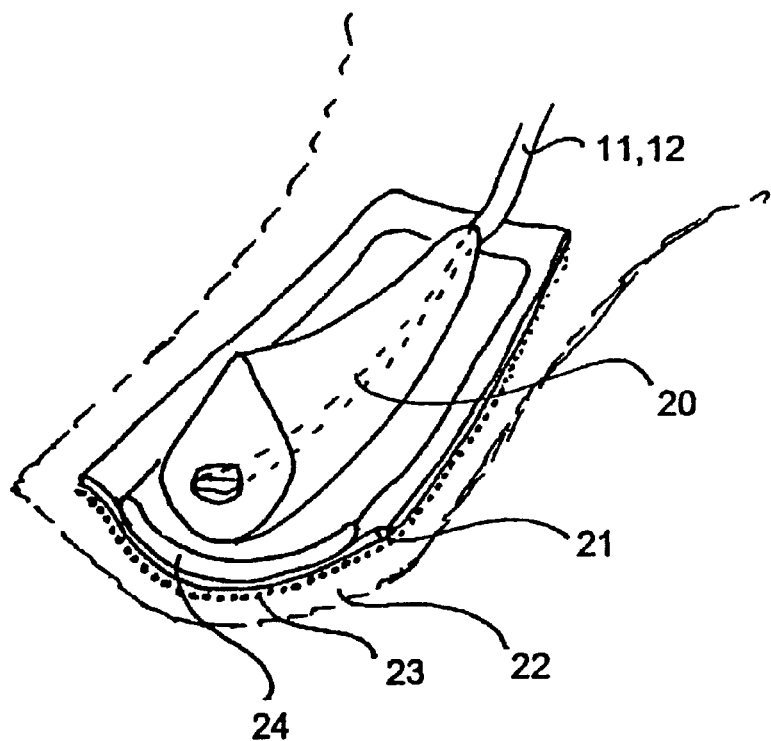
FIG. 4 is a partially schematic perspective illustration of a pad according to another embodiment.
Figure 6:
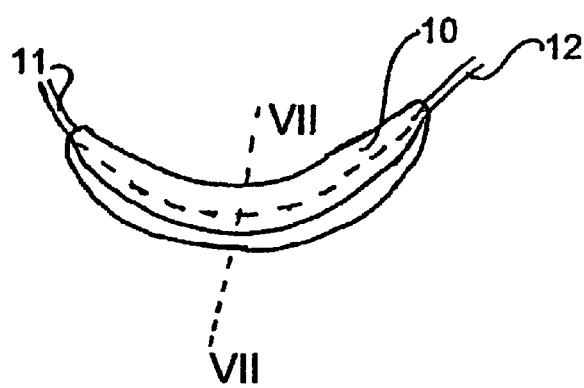
FIG. 6 is a side view of the pad of FIG. 1.
Figure 7A:
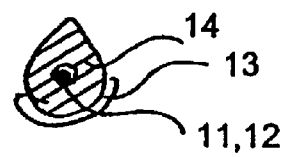
FIGS. 7A and 7B are cross-section of alternative structures of the pad of FIG. 6, taken on the plane VII-VII of FIG. 6.
Figure 7B:
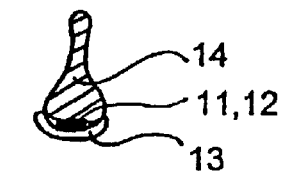
Figure 8:
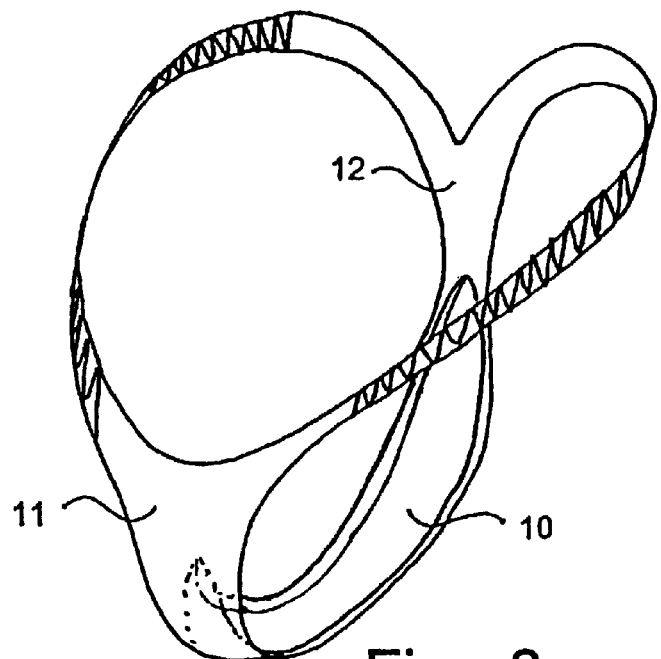
FIG. 8 is a perspective illustration of a pad according a further embodiment of the invention.

The pad of FIG. 1 is illustrated in side view in FIG. 6, in which only the initial part of the strings or ribbons 11, 12 are shown. Said strings or ribbons 11, 12, may be elastic ribbons contained in a tunnel-like cavity inside the absorbing matrix and drawn outside only when in use (FIGS. 7A and 4). The ribbon may also be placed between the absorbing matrix and the functional backing as shown in FIG. 7B, or may be an extended part of the absorbing matrix or functional backing. The combination of absorbing matrix 10 or 14, elastic holding ribbons 11 and 12, and the functional backing 13 may form an underwear-like structure (not unlike a G-string) as shown in FIG. 8.

Another embodiment is illustrated in FIG. 4. Herein the absorbing matrix and the functional backing are not connected together as in the embodiments of FIGS. 1 and 2. The absorbing matrix, indicated at 20, has an approximate banana-shape, as in the previous embodiment. The functional backing is a film of impermeable material 21, which is separate from the matrix 20. When the pad is applied to the body, the absorbing matrix is placed against the body area to be treated, the functional backing is placed so as to cover the absorbing matrix, viz. to the outside of it, and the whole assembly is held in place by an item of underwear, for instance, drawers, partially as shown at 22.

In a similar embodiment, the absorbing matrix is placed against the body area and the functional backing is placed and attached by an adhesive layer 23 to the underwear (as with hygienic pads). In this case, the functional backing may have on its inner side (the one facing the absorbing matrix) an extra layer of absorbing material (in this case, the combination of functional backing 21 with an adhesive layer 23 and an incorporated absorbing layer 24 making it a hygienic pad, as known in the art).

According to a further embodiment the absorbing matrix is placed against the body area and the functional backing is placed and attached by an adhesive layer to the underwear (as with hygienic pads).

In the preceding embodiments, the absorbing matrix is supposed to be saturated with the medicament solution. To maintain the pad sterile and to prevent evaporation of the solvent of the salts, the pad can be wrapped in an impermeable wrapping, e.g. a suitable plastic film. However pads so wrapped, comprising a saturated matrix, tend to have a short shelf life, since the impermeability of the wrapping is never absolute. Therefore, in some embodiments of the invention, the medicament is contained in an impermeable container, such as a bag of impermeable plastic film, which can be located within the matrix or on an surface, preferably the outer absorbing surface, between the absorbing matrix and the impermeable backing thereof, or could be an entirely separate component of the pad. In those embodiments, a release mechanism may be provided for releasing the medicament into the matrix when the pad is used. Such a release mechanism may comprise strings, bands, tapes or the like, connected or not to the attachment strings 11 and 12; or the bag may be such that it becomes ruptured at the moment the pad is used, e.g. by the pressure exerted on it to apply it to the desired surface of the body or by pressure otherwise applied to it.

Figure 5:
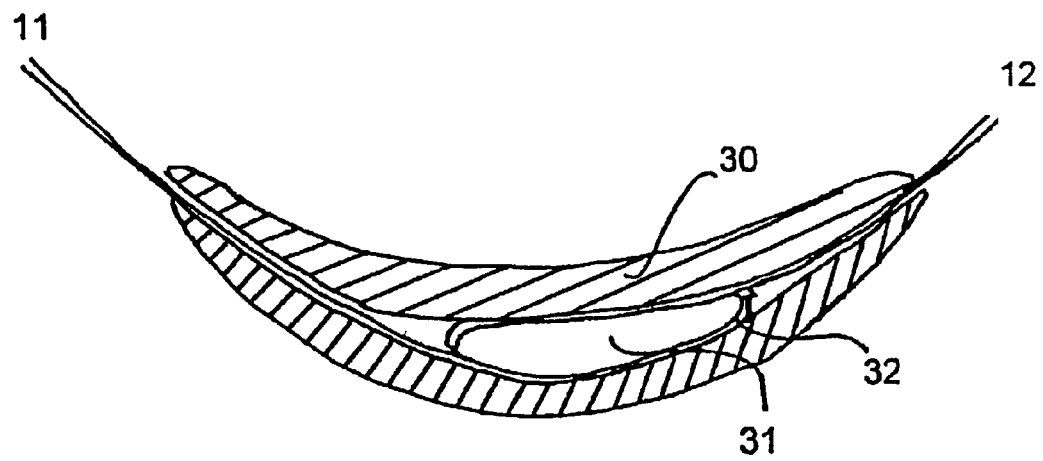
FIG. 5 is a schematic, longitudinal cross-section of a pad according to a further embodiment.

An example of such an embodiment is shown in FIG. 5, which constitutes a longitudinal cross-section of the absorbing matrix, designated herein by numeral 30, containing the medicament solution 31 inside a bag 32 of impermeable material, preferably constituted by a plastic film. Bag 32 should have such physical characteristics that it retains the medicament solution 31 as long as no pressure is applied to it, but when the pad is fitted to the body, the pressure applied to it will rupture it and permit the medical solution 31 to be absorbed into the matrix 30. The bag 32 may also be ruptured when the strings 11 and 12 that are attached to it are drawn outside. In this case, the end of string 11 may be attached (as in FIG. 5) to the far side (posterior, in this case) of the bag 32, and the end of string 12, to the anterior side of the bag. The functional backing is not shown in this embodiment, and it may be connected to the outer surface of the absorbing matrix or be separate from it, as shown in the previous embodiments.

The bag containing the medicament solution can also be separate from the absorbing matrix or can be attached to one surface, preferably the outer surface, thereof.

In another embodiment of the invention, not illustrated, the medicament can be applied to the matrix in dry form and water can be applied to it prior to using the pad, so as to dissolve the medicament and allow the solution to saturate the absorbing matrix. A dry medicament can be prepared by dissolving the medicament solution in a hydrophilic gel, such as Carbowax 950, Hyluronic acid, Agar-agar, etc., and then drying the gel or by lyophilization of the wet medicament containing absorbing matrix and leaving the solutes impregnate the matrix. In this embodiment, the patient may be asked to use the dry medicament absorbing matrix simply by applying it to a wetted body area that must be treated. Obviously, in this embodiment, the medicament containing bag 32 is not necessary. The dry medicament can also be separate from the absorbing matrix and can be placed thereon at the moment that the pad is used.

While some embodiments of the invention have been shown by way of illustration, it will be apparent that the invention can be carried out with many modifications, variations and adaptations, all without departing from its spirit or exceeding the scope of the claims.

The invention claimed is:

1. Pad for the treatment of hemorrhoidal inflammatory afflictions, which comprises:
    an absorbing matrix;
    a medicament that is a hypertonic substance;
    a functional backing for directing and limiting the activity of the medicament to a desired body surface; and
    an impermeable bag containing the medicament and being configured in a such a way so as to be ruptured when pressure is applied thereto permitting the medicament to be absorbed into the matrix,
    said pad being free from any supporting means that are attachable to male genitalia.
2. Pad according to claim 1, further comprising binding means for maintaining it in place and in engagement with the desired body surface.
3. Pad according to claim 2, wherein the binding means comprise strings or ribbons.
4. Pad according to claim 3, wherein the strings or ribbons carry adhesive members for binding them to an item of underwear or to the surface of the body.
5. Pad according to claim 2, wherein the binding means comprise complete underwear in a G-string like form.
6. Pad according to claim 1, wherein the medicament further comprises additives.
7. Pad according to claim 6, wherein the additives are chosen from among medically active components, steroids, minerals, vegetable or animal oils, or lubricants.
8. Pad according to claim 1, wherein the functional backing is made of impermeable material, that is sufficiently soft and pliable to adapt to the changes in shapes and contours of the human body and underwear.
9. Pad according to claim 8, wherein the impermeable material is a foil of a non-toxic, pliable metal alloy or other electrically conductive materials.
10. Pad according to claim 1, wherein the bag is made of impermeable plastic film, located within the matrix or on a surface thereof.
11. Pad according to claim 10, further comprising a release mechanism comprising strings, bands, tapes or the like, connected or not to the binding means for maintaining the pad in place.
12. Pad according to claim 1, wherein the absorbing matrix is impregnated with a desired solute.
13. Pad according to claim 12, wherein the absorbing matrix is coated with or made of hydrophilic gel, partially or completely dehydrated, containing the solute.
14. Pad according to claim 1, wherein the absorbing matrix is tubular or banana-shaped to conform to the perineum.
15. Pad according to claim 1, wherein the absorbing matrix and the functional backing are structurally connected.
16. Pad according to claim 1, wherein the absorbing matrix and the functional backing are separate.
17. Pad according to claim 1, wherein the absorbing matrix is made of cotton, lignin cellulose or synthetic absorbing materials.
18. Pad according to claim 1, wherein the medicament is a hypertonic solution of inorganic salts or of mixtures thereof.
19. Pad according to claim 1, wherein the inorganic salt solutions are chosen from among salts of alkali and/or earth-alkali metals and their mixtures.
20. Pad according to claim 1, wherein the inorganic salt solutions are comprised of Dead Sea salts and brines.
21. Pad according to claim 1, wherein the medicament saturates the absorbing matrix, but does not exceed its absorbing capacity, to avoid its leakage beyond the limits of the functional backing and of the surrounding skin.
22. Pad according to claim 1, wherein the functional backing is made of semipermeable materials.
23. Pad according to claim 1, wherein the functional backing is provided with an adhesive substance for adhesively retaining the absorbent matrix.
24. Pad according to claim 1, wherein the functional backing is provided with an adhesive substance for adhesively attaching the backing to an underwear.
25. Pad according to claim 1, wherein the functional backing has edges extending beyond the absorbing matrix.
26. Pad according to claim 1, wherein edges of the functional backing are provided on their inner side with a pressure-sensitive, bio-compatible adhesive.
27. Pad according to claim 1, wherein the absorbing matrix is thick and spongy to conform to irregular areas of the body.

* * * * *